United States Patent [19]
Boyd et al.

[11] Patent Number: 5,304,497
[45] Date of Patent: Apr. 19, 1994

[54] METHOD OF FORMING N-PROTECTED AMINO ACID THIOHYDANTOINS

[75] Inventors: Victoria L. Boyd, San Carlos; MeriLisa Bozzini; Piotr J. Guga, both of San Mateo; Gerald Zon, San Carlos, all of Calif.

[73] Assignee: Applied Biosystems, Inc., Foster City, Calif.

[21] Appl. No.: 914,280

[22] Filed: Jul. 15, 1992

Related U.S. Application Data

[63] Continuation-in-part of Ser. No. 775,771, Oct. 15, 1991, Pat. No. 5,185,266.

[51] Int. Cl.$^5$ .............................................. C07K 1/02
[52] U.S. Cl. .................................... 436/89; 530/345; 530/334; C07K/1/02
[58] Field of Search ..................... 436/86, 89, 90, 161; 548/318.5, 319.5; 530/345, 334

[56] References Cited

U.S. PATENT DOCUMENTS

| | | | |
|---|---|---|---|
| 4,173,563 | 11/1979 | Yamazaki et al. | 260/112.5 |
| 4,837,165 | 6/1989 | Hawke | 436/89 |
| 4,935,494 | 6/1990 | Miller | 530/345 |
| 4,965,343 | 10/1990 | Felix et al. | 530/334 |

OTHER PUBLICATIONS

Bannwarth, W., and Knorr, R., "Formation of Carboxamides with N,N,N',N'-Tetramethyl (Succinimido) Uronium Tetrafluoroborate in Aqueous Organic Solvent Systems," Tetrahedron Letters 32(9):1157–1160 (1991).

Dourtoglou, V., and Gross, B., "O-Benzotriazolyl-N,N,N',N'-Tetramethyluronium Hexafluorophosphate as Coupling Reagent for the Synthesis of Peptides of biological Interest," Synthesis 7:572–574 (1984).

Frerot, E., et al., "PyBOP® and PyBroP: Two Reagents for the Difficult Coupling of the α,α-Dialkyl Amino Acid, Aib.," Tetrahedron 47(2):259–270 (1991).

Hawke, D. H., et al., "Microsequence Analysis of Peptides and Proteins: Trimethylsilylisothiocyanate as a Reagent for COOH-Terminal Sequence Analysis," Anal. Biochem. 166:298–307 (1987).

Inglis, A. S., et al., "C-Terminal Sequencing: A New Look at the Schlack-Kumpf Thiocyanate Degradation Procedure," in *Methods in Protein Sequence Analysis* (Wittman–Liebold, B., ed.) Springer Verlag, 137–144 (1988).

Knorr, et al., "New Coupling Reagent in Peptide Chemistry," Tetrahedron Letters 30(15):1927–1930 (1989).

Meuth, J. L., et al., "Stepwise Sequence Determination from the Carboxyl Terminus of Peptides," Biochem. 21:3750–3757 (1982).

Miller, C. G., "Carboxyl-Terminal Sequence Analysis of Proteins and Peptides by Chemical Methods," in *Methods in Protein Sequence Analysis* (Wittman-n–Liebold, B., ed.) Springer Verlag, 145–151 (1988).

Parham, M. E., and Loudon, G. M., "Carboxyl-Terminal Sequential Degradation of Peptides," Biochem. Biophys. Res. Comm. 80(1):1–6 (1978).

Stark, G. R., "Sequential Degradation of Peptides and Proteins from Their COOH Termini with Ammonium Thiocyanate and Acetic Anhydride," in *Methods in Enzymology* (Hirs, C. H. W., et al., eds.), Academic Press, vol. 25, 369–384 (1972).

Tarr, G. E., "The Long Search for a Viable Method of C-Terminal Sequencing," in *Methods in Protein Sequence Analysis* (Wittman Liebold, B., ed.), Springer Verlag, 129–136 (1988).

*Primary Examiner*—James C. Housel
*Assistant Examiner*—David Redding
*Attorney, Agent, or Firm*—Joseph H. Smith; Peter J. Dehlinger

[57] ABSTRACT

A method of forming a thiohydantoin from an N-protected amino acid. The method employs a uronium or phosphonium compound to activate the terminal carboxyl group of the amino acid and a thiocyanate reagent to cyclize the activated amino acid to the thiohydantoin. The thiohydantoin can be cleaved from its N-protecting group, for use in C-terminal peptide sequencing. Particularly preferred uronium compounds include salts of 2-chlorouronium. Preferred thiocyanate reagents include trimethylsilyl isothiocyanate and crown ether adducts of metallothiocyanates, such as the 18-crown-6 adduct of KSCN.

14 Claims, 6 Drawing Sheets

↓ URONIUM SALT
  TMS-ITC

Fig. 5B

↓ XR₂BASE

Fig. 5C

↓ Substantially
  anhydrous TMS-ITC

Fig. 5D

+ Cleaved, modified thiohydantoin derivative

Fig. 5E

A15G: Fmoc-Ala-Lys-Gly-Lys-Gly-Lys-Leu-Tyr-Phe-Gly-Leu-Tyr-Gln-Phe-Gly

K11V: Lys-Gly-Lys-Gly-Lys-Gly-Val-Gln-Ala-Ile-Val

L20Y: Leu-Ile-Ala-Gln-Tyr-Leu-Ile-Lys-Gly-Lys-Gly-Lys-Gln-His-Tyr-Asn-Tyr-Phe-Leu-Tyr

K10A: Lys-Gly-Lys-Gly-Lys-Tyr-Ala-Leu-Met-Ala

K13Y: Lys-Gly-Lys-Gly-Lys-Gly-Gln-His-Tyr-Asn-Tyr-Trp-Leu-Tyr

K11(S)V: Lys-Gly-Lys-Gly-Lys-Gly-Val-Ala-Ser-Ala-Val

K12S: Lys-Gly-Lys-Gly-Lys-Gly-Gln-Val-Ala-Asn-Val-Ser

K13R: Lys-Gly-Lys-Gly-Lys-Gly-Gln-His-Tyr-Asn-Tyr-Arg-Leu-Tyr

K12V: Lys-Gly-Lys-Gly-His-Gly-Tyr-Met-Ile-Trp-Ala-Lys-Val

A14L: Fmoc-Ala-Lys-Gly-Lys-Gly-Lys-Gly-Phe-Tyr-Leu-Gly-Phe-Tyr-Leu

Fig. 6

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
       ( A ) LENGTH: 2 amino acids
       ( B ) TYPE: amino acid
       ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
       ( C ) INDIVIDUAL ISOLATE: test peptide ( x i ) SEQUENCE DESCRIPTION: SEQ ID NO:1:

Ala Ala
   1

( 2 ) INFORMATION FOR SEQ ID NO:2:

( i ) SEQUENCE CHARACTERISTICS:
       ( A ) LENGTH: 3 amino acids
       ( B ) TYPE: amino acid
       ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
       ( C ) INDIVIDUAL ISOLATE: test peptide ( x i ) SEQUENCE DESCRIPTION: SEQ ID NO:2:

Ala Ala Ala
   1

( 2 ) INFORMATION FOR SEQ ID NO:3:

( i ) SEQUENCE CHARACTERISTICS:
       ( A ) LENGTH: 14 amino acids
       ( B ) TYPE: amino acid
       ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
         ( C ) INDIVIDUAL ISOLATE: A14G ( x i ) SEQUENCE DESCRIPTION: SEQ ID NO:3:

Ala Lys Gly Lys Gly Lys Leu Phe Tyr Gly Leu Phe Tyr Gly
1               5                   10

( 2 ) INFORMATION FOR SEQ ID NO:4:

( i ) SEQUENCE CHARACTERISTICS:
         ( A ) LENGTH: 12 amino acids
         ( B ) TYPE: amino acid
         ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
         ( C ) INDIVIDUAL ISOLATE: G12Y ( x i ) SEQUENCE DESCRIPTION: SEQ ID NO:4:

Gly Ala Pro Lys Gly Lys Gly Lys Tyr Phe Leu Tyr
1               5                   10

( 2 ) INFORMATION FOR SEQ ID NO:5:

( i ) SEQUENCE CHARACTERISTICS:
         ( A ) LENGTH: 15 amino acids
         ( B ) TYPE: amino acid
         ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
         ( C ) INDIVIDUAL ISOLATE: A15G ( x i ) SEQUENCE DESCRIPTION: SEQ ID NO:5:

Ala Lys Gly Lys Gly Lys Leu Tyr Phe Gly Leu Tyr Gln Phe Gly
1               5                   10                  15

( 2 ) INFORMATION FOR SEQ ID NO:6:

( i ) SEQUENCE CHARACTERISTICS:
         ( A ) LENGTH: 11 amino acids
         ( B ) TYPE: amino acid
         ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
         ( C ) INDIVIDUAL ISOLATE: K11V ( x i ) SEQUENCE DESCRIPTION: SEQ ID NO:6:

Lys Gly Lys Gly Lys Gly Val Gln Ala Ile Val
1               5                   10

( 2 ) INFORMATION FOR SEQ ID NO:7:

( i ) SEQUENCE CHARACTERISTICS:
   ( A ) LENGTH: 20 amino acids
   ( B ) TYPE: amino acid
   ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
   ( C ) INDIVIDUAL ISOLATE: L20Y ( x i ) SEQUENCE DESCRIPTION: SEQ ID NO:7:

Leu Ile Ala Gln Tyr Leu Ile Lys Gly Lys Gly Lys Gln His Tyr Asn
1               5                   10                  15

Tyr Phe Leu Tyr
         20

( 2 ) INFORMATION FOR SEQ ID NO:8:

( i ) SEQUENCE CHARACTERISTICS:
      ( A ) LENGTH: 10 amino acids
      ( B ) TYPE: amino acid
      ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
      ( C ) INDIVIDUAL ISOLATE: K10A ( x i ) SEQUENCE DESCRIPTION: SEQ ID NO:8:

Lys Gly Lys Gly Lys Tyr Ala Leu Met Ala
1               5                   10

( 2 ) INFORMATION FOR SEQ ID NO:9:

( i ) SEQUENCE CHARACTERISTICS:
      ( A ) LENGTH: 13 amino acids
      ( B ) TYPE: amino acid
      ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
      ( C ) INDIVIDUAL ISOLATE: K13Y ( x i ) SEQUENCE DESCRIPTION: SEQ ID NO:9:

Lys Gly Lys Gly Lys Gln His Tyr Asn Tyr Trp Leu Tyr
1               5                   10

( 2 ) INFORMATION FOR SEQ ID NO:10:

( i ) SEQUENCE CHARACTERISTICS:
      ( A ) LENGTH: 11 amino acids
      ( B ) TYPE: amino acid
      ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
      ( C ) INDIVIDUAL ISOLATE: K11(S)V ( x i ) SEQUENCE DESCRIPTION: SEQ ID NO:10:

Lys Gly Lys Gly Lys Gly Val Ala Ser Ala Val
1               5                   10

( 2 ) INFORMATION FOR SEQ ID NO:11:

( i ) SEQUENCE CHARACTERISTICS:
      ( A ) LENGTH: 11 amino acids
      ( B ) TYPE: amino acid
      ( D ) TOPOLOGY: linear    ( i i ) MOLECULE TYPE: protein    ( i i i ) HYPOTHETICAL: NO    ( i v ) ANTI-SENSE: NO    ( v i ) ORIGINAL SOURCE:
      ( C ) INDIVIDUAL ISOLATE: K12S    ( x i ) SEQUENCE DESCRIPTION: SEQ ID NO:11:

Lys Gly Lys Gly Lys Gly Val Ala Ser Ala Val
1               5                   10

( 2 ) INFORMATION FOR SEQ ID NO:12:

( i ) SEQUENCE CHARACTERISTICS:
      ( A ) LENGTH: 13 amino acids
      ( B ) TYPE: amino acid
      ( D ) TOPOLOGY: linear    ( i i ) MOLECULE TYPE: protein    ( i i i ) HYPOTHETICAL: NO    ( i v ) ANTI-SENSE: NO    ( v i ) ORIGINAL SOURCE:
      ( C ) INDIVIDUAL ISOLATE: K13R    ( x i ) SEQUENCE DESCRIPTION: SEQ ID NO:12:

Lys Gly Lys Gly Lys Gln His Tyr Asn Tyr Arg Leu Tyr
1               5                   10

( 2 ) INFORMATION FOR SEQ ID NO:13:

( i ) SEQUENCE CHARACTERISTICS:
      ( A ) LENGTH: 12 amino acids
      ( B ) TYPE: amino acid
      ( D ) TOPOLOGY: linear    ( i i ) MOLECULE TYPE: protein    ( i i i ) HYPOTHETICAL: NO    ( i v ) ANTI-SENSE: NO    ( v i ) ORIGINAL SOURCE:
      ( C ) INDIVIDUAL ISOLATE: K12V    ( x i ) SEQUENCE DESCRIPTION: SEQ ID NO:13:

Lys Gly Lys Gly His Tyr Met Ile Trp Ala Lys Val
1               5                   10

( 2 ) INFORMATION FOR SEQ ID NO:14:

( i ) SEQUENCE CHARACTERISTICS:
      ( A ) LENGTH: 14 amino acids
      ( B ) TYPE: amino acid
      ( D ) TOPOLOGY: linear    ( i i ) MOLECULE TYPE: protein (i i i) HYPOTHETICAL: NO (i v) ANTI-SENSE: NO (v i) ORIGINAL SOURCE:
  (C) INDIVIDUAL ISOLATE: A14L (x i) SEQUENCE DESCRIPTION: SEQ ID NO:14:

Ala Lys Gly Lys Gly Lys Gly Phe Tyr Leu Gly Phe Tyr Leu
1               5                   10

METHOD OF FORMING N-PROTECTED AMINO ACID THIOHYDANTOINS

The present invention is a continuation-in-part of co-pending U.S. patent application Ser. No. 07/775,771, filed Oct. 15, 1991, now U.S. Pat. No. 5,185,266.

FIELD OF THE INVENTION

The present invention relates to methods of synthesizing amino acid thiohydantoin.

CITED REFERENCES

Bannwarth, W., Tetrahedron Letters, 32, 1157–1160 (1991).
Boyd et al , U.S. patent application Ser. No. 07/775,771, U.S. Pat. No. 5,185,266.
Boyd et al., U.S. Pat. No. 5,051,368.
Boyd, V., Tetrahedron Letters, 31, 3849–3852 (1990).
Doutogolu, V., Synthesis, 572–574 (1984).
Frerot, E., Tetrahedron Letters, 47, 259–270 (1991).
Gokel, G., Synthesis, 168–184 (1976).
Hawke, U.S. Pat. No. 4,837,165.
Hawke et al., U.S. Pat. No. 5,049,507.
Hawke, D. H. et al., *Anal Biochem,* 166:298 (1987).
Inglis, A. S., et al., in *Methods in Protein Sequence Analysis* (Wittmann-Liebold, B., ed.) Springer Verlag, 137–144 (1988).
Knorr, R , Tetrahedron Letters, 30, 1927–1930 (1989).
Meuth, J., et al., *Biochemistry,* 21:3750 (1982).
Miller, U.S. Pat. No. 4,935,494.
Miller, C. G., et al., in *Methods in Protein Sequence Analysis* (Wittmann-Liebold, B., ed.) Springer Verlag, 145–151 (1988).
Newman, A. A., ed. in *Chemistry and Biochemistry of Thiocyanic Acid and its Derivatives* (Academic Press, 1975), p 8.
Parham, et al., *Biochem Biophys Res Comm,* 80(1):1 (1978).
Reed, M., et al., Chemical Reviews, vol. 8, p. 1721 (1991).
Stark, G. R., *Biochemistry,* 7(5):1796–1807 (1968).
Tarr, G. E., in *Methods in Protein Sequence Analysis* (Wittmann-Liebold, B., ed.) Springer Verlag, 129–136 (1988).

BACKGROUND OF THE INVENTION

A variety of chemical-reaction methods for converting N-protected amino acids, including the C-terminal amino acid residues of peptides, to a corresponding thiohydantoin (TH) have been proposed TH formation is useful, for example, in C-terminal amino acid sequencing, where a C-terminal amino acid of a peptide is sequentially (a) converted to its corresponding TH, (b) cleaved from the remaining peptide, and (c) identified as to amino acid, e.g., by HPLC. Another use of such reaction methods is in preparing amino acid TH compounds for use as standards, e.g., in C-terminal sequencing.

The conversion of protected amino acids to corresponding amino acid TH's was first proposed in 1011 by T. B. Johnson et al. (J. Am. Chem. Soc., 48:103 (1911), and in 1926 by Schlack and Kumpf [Hoppe-Seyder's Z Phys Chem, 154:125 (1926)]. A number of improvements to this early method have since been proposed (see, e.g., Stark; Boyd et al., U.S. Pat. No. 5,051,368; Hawke, 1987; Hawke, U.S. Pat. No. 4,837,165; Hawke et al., U.S. Pat. No. 5,049,507; Inglis; Miller, 1988; and Miller, U.S. Pat. No. 4,935,494).

Stark's chemistry for making 2-thiohydantoins often results in low yields and derivatized products (i.e. acetylation and dehydration). Also, Hawke et al., (U.S. Pat. No. 5,049,507) propose a method of forming a peptidyl-TH in which an acyl-isothiocyanate moiety is used to generate the thiohydantoin. However, this method has the same limitations as are generally associated with acetylation of the terminal carboxyl group (Stark), e.g., degradation of the amino acid side chains of the peptide. Recent efforts to improve thiohydantoin-based methods have focused on improving the efficiency of forming the C-terminal activated ester. For example, Boyd et al. (U.S. Pat. No. 5,051,368) propose a method of forming a C-terminal thiohydantoin that employs N-substituted ketenimines, as generated by Woodward's Reagent K, to form the activated ester.

SUMMARY OF THE INVENTION

An object of the present invention is to provide an improved method of converting an N-protected amino acid to the corresponding amino acid thiohydantoin. The method includes reacting the N-protected amino acid with a halouronium, pseudohalouronium, triflate uronium, or sulfonyl uronium compound, or with a halophosphonium, pseudohalophosphonium, tosylphosphonium, triflate phosphonium, or sulfonyl phosphonium compound, and a thiocyanate reagent under conditions effective to form the amino acid thiohydantoin.

In a preferred embodiment, the reaction of the amino acid with the uronium or phosphonium compound is carried out in the presence of the thiocyanate reagent. In various preferred embodiments, the uronium compound is a 1,1,3,3-tetrasubstituted 2-halouronium salt, e.g., 1,1,3,3,-tetramethyl 2-chlorouronium chloride, 4,5-dihydro, 1,3-dimethyl 2-chloro imidazolium chloride, or bispyrrolidino chlorouronium tetrafluoroborate, and the phosphonium compound is a P-halophosphonium salt, e.g., usually tris(dialkylamino) phosphonium salt such as tris(pyrrolidino)-bromo phosphonium hexafluoro phosphate.

The thiocyanate reagent may be a silylisothiocyanate, such as trimethylsilyl-isothiocyanate, a pyridinium thiocyanate, or an adduct of macrocyclic ether or a metallothiocyanate, such as an 18-crown-6 adduct of a thiocyanate salt of a monovalent cation.

In one aspect, the method is used for C-terminal amino acid sequencing. The method includes, after TH formation of a C-terminal amino acid residue, according to the method described above, contacting the formed amino acid TH with a cleaving reagent effective to release a deprotected amino acid thiohydantoin from residual peptide, as described below; and isolating and identifying the deprotected amino acid thiohydantoin, to identify the cleaved C-terminal residue of the polypeptide.

The invention further includes, in a method of forming a thiohydantoin from an N-protected amino acid residue, which includes the step of reacting the residue with a carboxyl activating agent, and with an thiocyanate, the improvement of employing as the thiocyanate, a crown ether adduct of a metallothiocyanate.

These and other objects and features of the invention will become more fully apparent when the following detailed description of the invention is read in conjunction with the accompanying drawings.

DETAILED DESCRIPTION OF THE INVENTION

A. Definitions

Figure 1A:
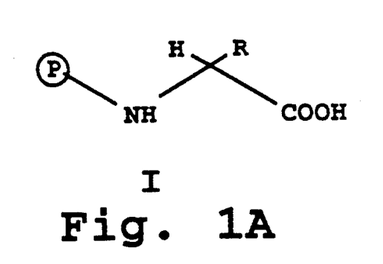
FIGS. 1A–1C show the structures of an N-protected amino acid (1A), a protected amino acid thiohydantoin (1B), and a deprotected amino acid thiohydantoin (1C), as defined herein.

The following terms, as used herein, have the indicated meanings:

"N-protected amino acid" refers to an amino acid, including a polypeptide, having a protecting group bonded to its N-terminus. Typical protecting groups include Fmoc, Boc, acyl, polypeptidyl groups, and covalently bonded surfaces, as are well-known. As referred to herein, an N-protected amino acid can optionally be bound to a solid phase support—as a N-terminal amino group or as through a side chain, e.g., the $\epsilon$-amino group of lysine residue. A structural formula for an N-protected amino acid is shown in FIG. 1A, where the circled P represents a protecting group. The amino acid, whose side chain is represented by R, may have additional protection groups at amine, acid, sulfhydryl, or hydroxyl groups of the amino acid side chain.

"Peptide" or "polypeptide" refers to peptides, including native or denatured proteins. In FIG. 1A, the protected amino acid is a C-terminal residue of a peptide if the protecting group (the circled P) includes one or more amino acid residues coupled to the C-terminal residue through an amide bond.

Figure 1B:
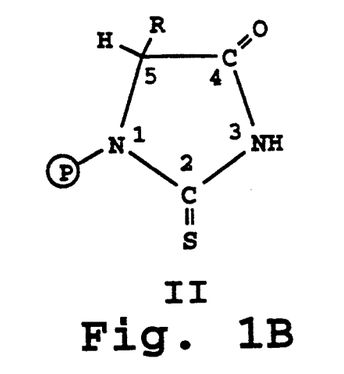
Figure 1C:
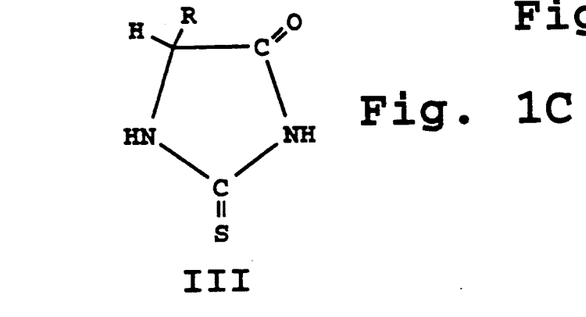

"Amino acid thiohydantoin" or "amino acid TH" refers to members of the class of compounds having the structural formula shown in FIG. 1B, where R is an associated side chain of an amino acid, and the numerals indicate the conventional numbering scheme for the thiohydantoin. In accordance with the present invention as described herein, a thiohydantoin is formed from an N-protected amino acid, which may include an N-protected free amino acid or the C-terminal amino acid of a peptide. As used herein, an amino acid TH can have an N-protecting group, as shown at II in FIG. 1, or can be deprotected, i.e., released from its N-protecting group, as shown in FIG. 1C.

"Acyl thiohydantoin" refers to members of the class of compounds having the formula shown at II in FIG. 1B, where the group indicated by the circled P is an acyl Typically, P—C(O)— is an N-protected amino acid residue, including a polypeptide, which can optionally be bound to a solid phase support, as through a side-chain or N-terminal amino group. An acyl thiohydantoin is often referred to herein as an "N-protected thiohydantoin", "peptidyl thiohydantoin", "C-terminal peptidyl thiohydantoin", and the like. The amide bond linking the acyl group to the thiohydantoin ring nitrogen ($N_1$) is referred to herein as an "acyl-thiohydantoin bond" or "peptidyl-thiohydantoin bond", and the like.

"Isothiocyanate reagent" or "thiocyanate reagent" refers to a chemical species that provides a thiocyanate [SCN] anion.

"Solid support" or "solid phase support" refers to any solid support that has surface functionality or can be derivatized to have surface functionality. Preferably, the surface functionality can interact with an amine group of a peptide so as to attach the peptide to the support. Such attachment can be by covalent linkage, ionic interactions, and/or hydrophobic interactions. Exemplary solid supports include, but are not limited to, sepharose, aminopropyl derivative of silica, aminopropyl-CPG (controlled pore glass), aminoethyl cellulose, Tris-aryl$^R$-NH, glass beads, polyacrylamide particles, 1,4-phenylene (DITC) diisothiocyanate glass, functionalized polystyrene, polyethylene, membrane supports such as functionalized PVDF, and the like.

Figure 4A:
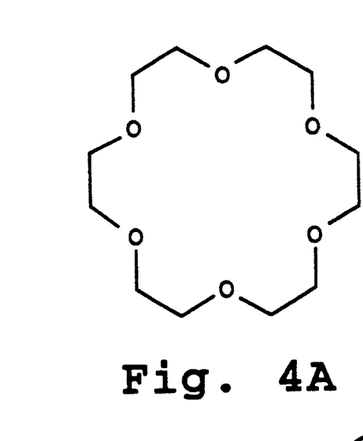
FIGS. 4A–4C show exemplary 18-crown-6 ethers (4A and 4B) and a complex of KSCN with an 18-crown-6 ether.
Figure 4B:
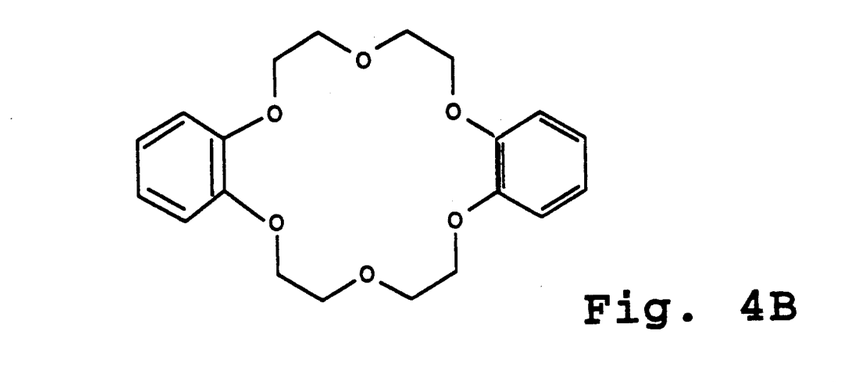

"Crown ether" refers to cyclic compounds of the form $-(Y-CH_2-CH_2-)_n$ where Y is a heteroatom like O, S or N, and n is typically 4–8. The compounds form a crown-like structure in which the heteroatoms form the "tips" of a crown. FIGS. 4A and 4B show typical 18-crown-6 ethers, so named by the fact that the ring structure has a total of 18 atoms, including 6 heteroatoms.

Figure 4C:
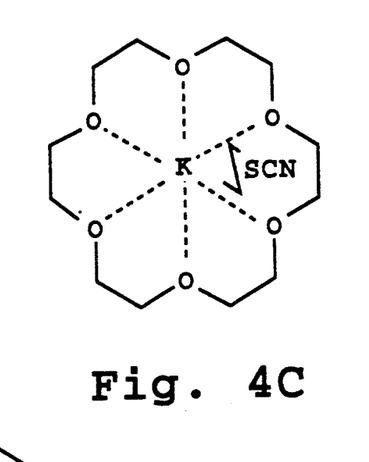

A "metallothiocyanate complex of a crown ether" refers to a complex of a metallothiocyanate, such as KSCN, NaSCN, CsSCN, or the like, in which the metal ion is complexed in the "hole" defined by the heteroatoms of the crown ether, as illustrated in FIG. 4C for the KSCN complex of an 18-crown-6 ether.

Figure 2:
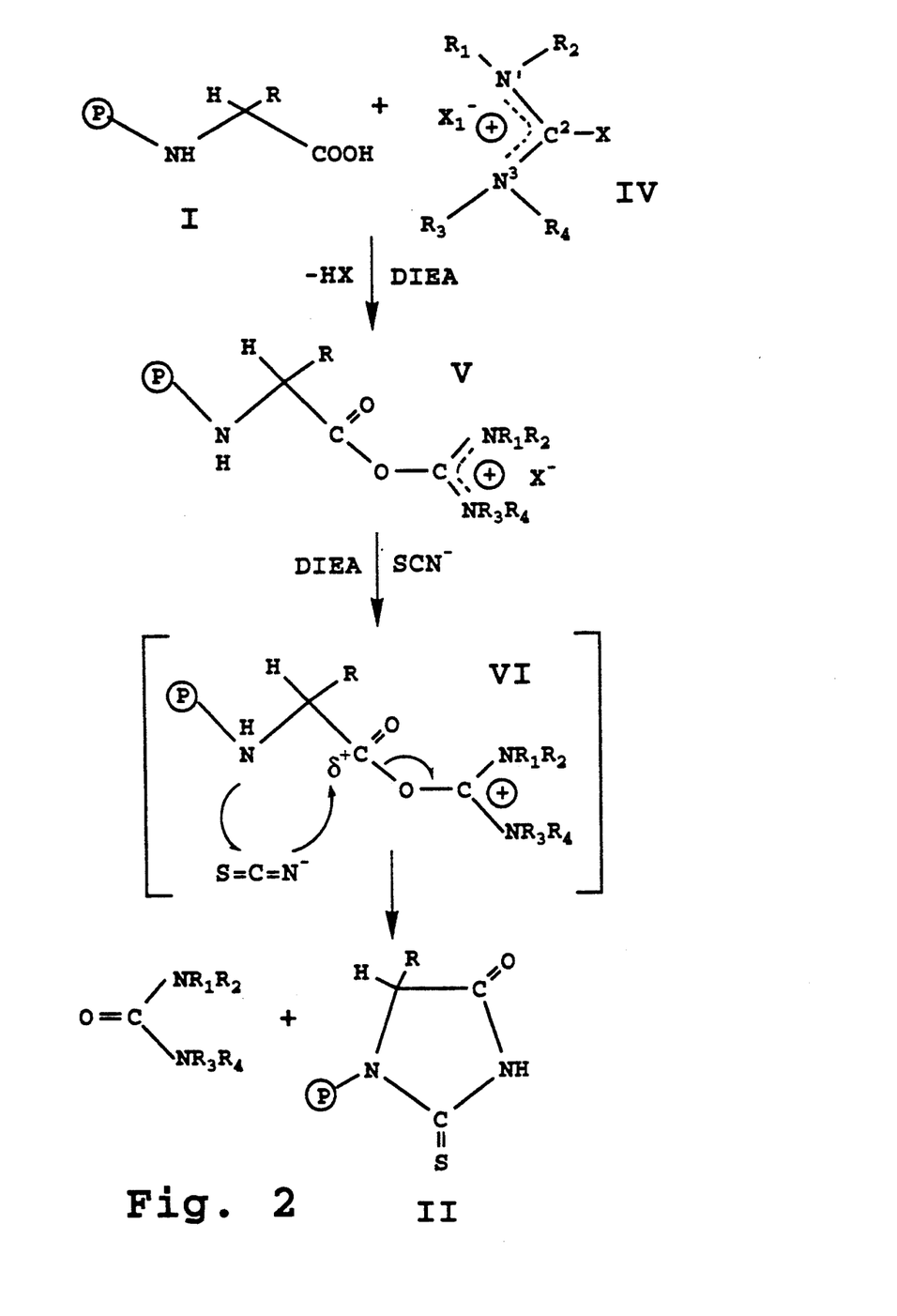
FIG. 2 shows a reaction scheme of the present invention in which a uronium compound (IV) is reacted with an N-protected amino acid (I) to give an N-protected thiohydantoin (II) via a proposed activated ester intermediate.

A "uronium compound" refers to a compound having the general structure shown at IV in FIG. 2. Uronium compounds which are useful in the present invention are those in which X is a halogen, pseudohalogen, such as cyanide, azide, cyanate, thiocyanate, selenocyanate, and tellurocyanate (Newman), or sulfonate group, such as tosylate (p-toluene sulfonate), triflate (triflouoromethane sulfonate), or sulfonate itself.

Figure 3:
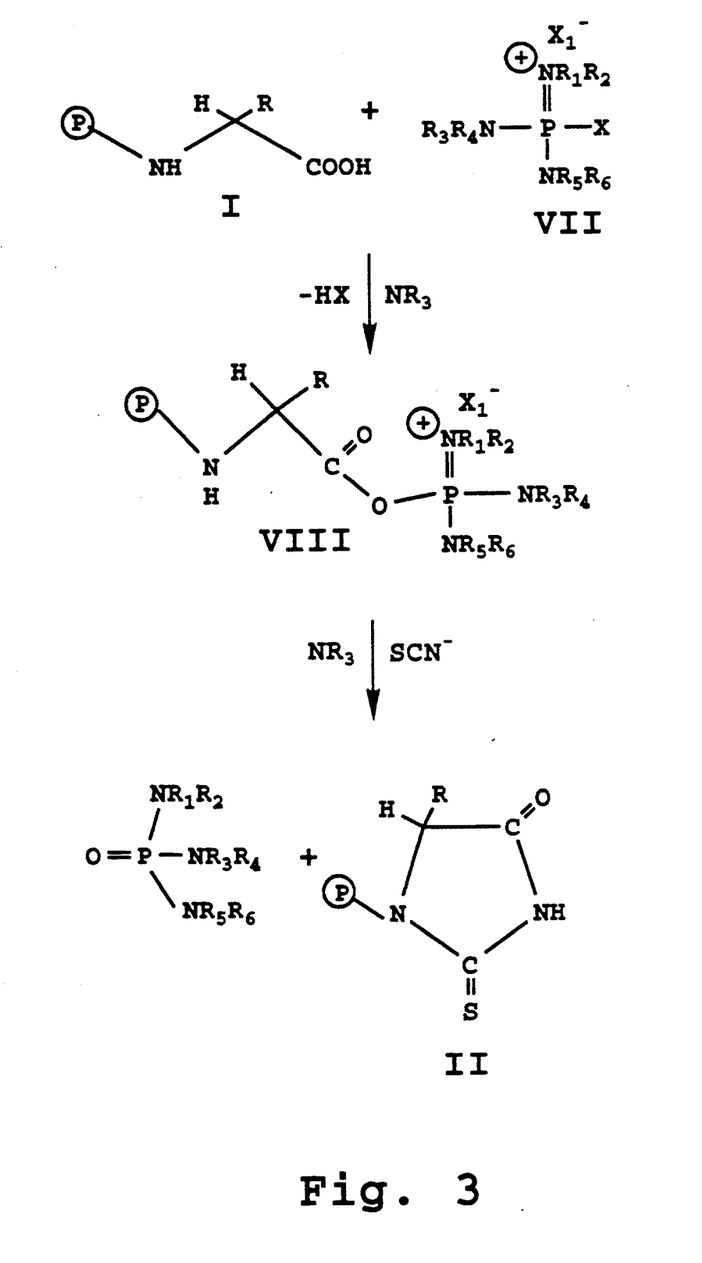
FIG. 3 shows a reaction scheme of the present invention in which a phosphonium (VII) compound is reacted with an N-protected amino acid (I), e.g., a polypeptide, to form an N-protected amino acid thiohydantoin (II)

A "phosphonium compound" refers to a compound having the general structure shown at VII in FIG. 3. Phosphonium compounds which are useful in the present invention are those in which X is a halogen, pseudohalogen, or sulfonate groups, such as tosyl, triflate, or sulfonate itself.

B. Formation of Amino Acid Thiohydantoin

In practicing the invention, an N-protected amino acid is reacted with a uronium or phosphonium salt, typically in a nonaqueous medium, and further reacted with a thiocyanate reagent to form the corresponding amino acid TH or peptidyl TH. In the reaction, the uronium or phosphonium compound is hypothesized to form an activated derivative, meaning a reactive uronium ester or phosphonium mixed anhydride, of the terminal carboxyl group of the amino acid, which then reacts with a thiocyanate reagent to complete the reaction leading to formation of the TH. The derivative is said to be "activated", in the context of the present invention, because it is reactive with a thiocyanate reagent, whereas the terminal carboxyl (underivatized) group of the amino acid does not react with thiocyanate anion.

The reaction is illustrated for a uronium salt in FIG. 2. As shown in this figure, reaction of N-protected amino acid (I) with a uronium salt (IV) leads to an activated ester, such as the intermediate V shown in FIG. 2, with the substitution of the X group. Studies conducted in support of the present invention indicate that the group X in the uronium or phosphonium compound must be a good leaving group and at the same time, not have the ability to displace the uronium or phosphonium group in the activated ester, except where X is itself thiocyanate, in which case the TH may be formed by the uronium or phosphonium compound alone.

Example 1B, for instance, illustrates a reaction in which the uronium compound employed is HBTU (2-(1H-benzotriazol-1-yl)-1,1,3,3-tetramethyluronium hexafluorophosphate, i.e., where X is a benzotriazole group. This reaction gave poor TH yields with a variety of peptide C-terminal residues, presumably because of reaction of the HOBt leaving group with the chlorouronium ester to produce a HOBt ester that is less reactive with SCN in forming a thiohydantoin.

X groups which are both good leaving groups, and do not interfere with the activated derivative, include halogen atoms, such as chlorine, bromine and fluorine, iodine, and pseudohalogens, and sulfonic acid and sulfonic acid derivatives, including toluene sulfonate and triflate.

Preferred uronium compounds include 2-halouronium compounds, such as compounds having the formula shown at IV in FIG. 2, where $R_1$, $R_2$, $R_3$, $R_4$ are each alkyl, aryl, or alkaryl groups, and X is a halogen or other suitable leaving group. Since the uronium species is positively charged, a negatively charged counterion, such as halide, tetrafluoroborate, hexafluorophosphate, and the like, is present.

One preferred uronium compound is a 2-halouronium salt, and more preferably, is a 2-chlorouronium salt. Also preferred is a tetraalkyl uronium compound, such as an N,N,N',N'-tetramethyl uronium species. A particularly preferred uronium salt is 1,1,3,3-tetramethyl-2-chlorouronium chloride (TMUCl), which can be synthesized by the method of Knorr et al., *Tetrahedron Letters*, 30(24):1927 (1989).

Other preferred uronium compounds include an N,N'-dicyclo compound, such as bistetrahydropyrrolochlorouronium (TPyClU) tetrafluoroborate, which is available from SNPE, Inc. (Princeton, N.J.). Also, an N,N'-monocyclo compound can be employed, such as the 1,3-dimethyl-1,3-ethyleno chlorouronium salt formed from 1,3-dimethyl-2-imidazolidinone, using the method of Knorr et al.

With continued reference to FIG. 2, the activated uronium ester intermediate is hypothesized to undergo nucleophilic attack at the carbon atom of the derivatized carboxyl group by the thiocyanate reagent. The activation step to form the activated intermediate makes the carboxyl carbon a more electropositive carboxyl carbon, and thus more susceptible to nucleophilic attack. FIG. 2 shows one possible reaction mechanism for reaction with the thiocyanate reagent, in which the electronegative nitrogen atom of the thiocyanate reagent attacks at the carboxyl carbon and then cyclizes through the N atom of the target amino acid to form an N-protected thiohydantoin. This mechanism would proceed through an intermediate such as proposed at VI in FIG. 2.

The final reaction product, shown at II in FIG. 2, is an N-protected amino acid TH, with release of a tetraalkyl urea compound. When the N-protecting group is a peptidyl residue the thiohydantoin at II in FIG. 2 is said to be a "peptidyl thiohydantoin".

The reaction of the N-protected amino acid with the 2-halouronium salt is preferably carried out in the presence of the thiocyanate reagent, for enhanced yields of the TH. However, the formation of TH from the amino acid can be performed in stepwise fashion, if desired. Stepwise reaction may in some cases be desirable, especially if evidence exists that the uronium reagent is affecting the nature of the TH formed from the amino acid.

Activation of an N-protected amino acid by a uronium compound is typically performed under anhydrous solvent conditions. Polar, aprotic solvents are particularly preferred, such as acetonitrile, methylene chloride, and ethereal solvents. Also, use of a base is required to promote the reaction and improve yields. Preferred bases include tertiary amines, such as diisopropylethylamine (DIEA), triethylamine (TEA) and pyridine and its derivatives, such as 2,6-dimethyl pyridine.

The thiohydantoin formation reaction from the N-protected amino acid typically occurs over about 1–30 minutes at about 25°–60° C. For example, activation of most amino acids proceeds smoothly over the course of about 5–10 minutes at room temperature to 55° C. By contrast, TH formation by activation with acetic anhydride (Stark chemistry) typically requires at least 30 minutes reaction at about 60°–80° C.; and activation with Woodward Reagent K (which must be carried out at near room temperature) typically requires several hours. Thus, an important advantage of the present method is the greater ease of activation and TH formation, as measured by substantially lower reaction temperature and/or reaction time.

In solution, the molar ratio of uronium compound to amino acid employed is preferably about 1:1, and the ratio of thiocyanate reagent to amino acid is about 1:1, or greater.

Preferred thiocyanate reagents for use in the present invention include silylisothiocyanates, pyridinium thiocyanates, and metallothiocyanates. Particularly preferred silylisothiocyanates include trimethylsilyl-isothiocyanate (TMS-ITC). Particularly preferred metallothiocyanates include those that are commercially available, such as LiSCN, NaSCN, KSCN, RbSCN, AgSCN, and Hg(SCN)$_2$, and particularly monovalent thiocyanates of monovalent metals, such as NaSCN and KSCN.

According to one discovery herein, it was observed that metallothiocyanates themselves react very poorly in converting an activated amino acid to the corresponding TH. However, when complexed with a suitable crown ether, the metallothiocyanates can efficiently form TH compounds in the reaction method of the invention. This effect may be due, in part, to a solvation effect and/or an ion-pair effect (Gokel).

FIGS. 4A and 4B show the structural formulae for two 18-crown-6 ethers, which are particularly preferred for complexation with KSCN. The name 18-crown means the macrocycle contains a total of 18 atoms in the ring and 6 oxygen atoms. Preferred crown ethers for use in forming adducts of a metallothiocyanate include 12-crown-4, 15-crown-5, 18-crown-6, dibenzo-18-crown-6, and dibenzo-24-crown-8, which are commercially available from Aldrich Chemical (Milwaukee, Wis.). The particular metallothiocyanate salt which is employed in association with the crown ether can be selected on the basis of known cavity-size effects of various known ethers, as has been reported (Gokel). For example, the hole in 18-crown-6 ether has been estimated to be 2.6–3.2 Å, and the ionic diameter of $K^+$ is about 2.66 Å. Thus, the 18-crown-6 ether forms very stable complexes with potassium salts, such as KSCN.

The water sensitivity of the metallothiocyanates also appears to be reduced relative to silyl isothiocyanates, and the compounds are less corrosive. Also the reagent is convenient and safe, and stable over a several-day period.

A reaction analogous to the one described for a uronium compound can be carried out by reaction of the protected amino acid with a phosphonium compound. As shown in FIG. 3, a phosphonium compound (VII) reacts with an N-protected amino acid (I) to form an activated mixed anhydride, such as the structure proposed at VIII in FIG. 3, which reacts with $S=C=N^-$ anion of the thiocyanate reagent to generate the amino acid TH (II).

Phosphonium compounds which are positively charged that can be used to practice the invention are those having a good leaving group (e.g. halogen, pseudohalogens, and sulfonic acid groups, including P-toluene sulfonate and triflate groups), and which are capable of forming a phosphoro-carboxyl mixed anhydride from the carboxyl group of an N-protected amino acid. Preferred phosphonium compounds in this regard include P-halophosphonium salts. Exemplary phosphonium compounds include tris(dialkylamino)- and tris(pyrrolidino)-P-halophosphonium salts. Particularly preferred in this regard is bromo-tris(pyrrolidino)-phosphonium hexafluorophosphate (PyBroP TM), which is available from CalBiochem (La Jolla, Calif.). Again, the associated anion of the phosphonium species can be any anion that does not significantly interfere with the reaction, such as tetrafluoroborate, hexafluorophosphate, and the like.

Typical reaction conditions for forming a TH from a free amino acid in solution are given in Example 1. Examples 2–5, described below, also illustrate the method of the invention, but applied to the C-terminal amino acid of an immobilized peptide. The solution examples illustrates the use of the method for forming free amino acid THs for use, for example, as TH standards for HPLC identification of amino acid THs.

C. Application of the Method to C-Terminal Sequencing

Another application of the method of the invention is for use in C-terminal amino acid sequencing. In this method, the N-protected amino acid which is to be converted to the amino acid TH is the C-terminal amino acid residue of the peptide. The sequencing procedure can be adapted for automated or semi-automated operation, as will be described below.

A C-terminal sequencing method, in accordance with one aspect of the invention, is illustrated in FIGS. 5A–5E. The figures show a peptide 10 which is coupled at its N terminus or an internal lysine side chain via the ε-amino group, to a solid support 12. The solid support can be prepared with any surface functional group through which one can bind the polypeptide, including functional groups placed on the surface by chemical derivatization. For instance, the solid support can be a particle bead having surface amine groups that are suitably derivatized to serve as a site of attachment, e.g., with a bifunctional crosslinking reagent such as disuccinimidyl suberate, although any of a variety of methods for coupling a peptide to a solid support can be employed. A typical coupling reaction is described in Example 2A.

Figure 5A:
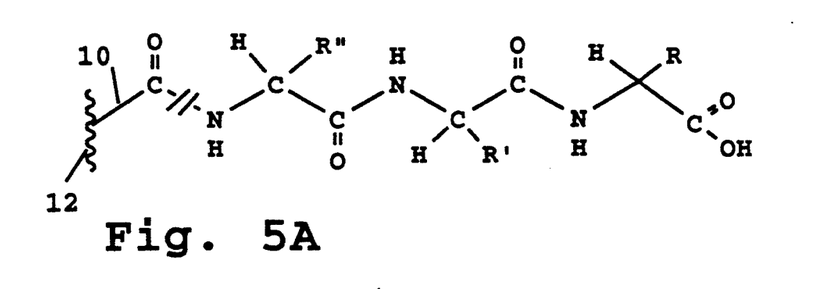
FIGS. 5A–5E illustrates how the method of the invention may be employed in a C-terminal peptide-sequencing method.
Figure 5B:
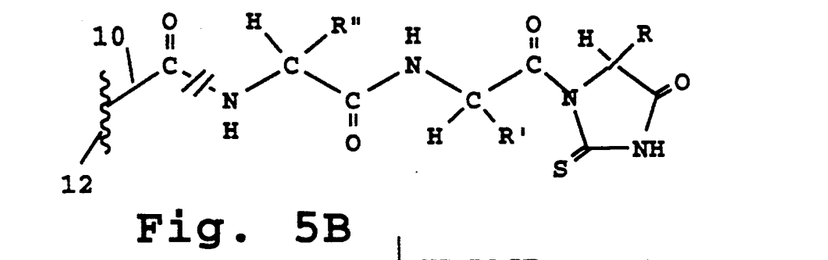

In the first step of the method, the immobilized peptide is reacted with a uronium or phosphonium compound in the presence of a thiocyanate reagent, as described in Section B, to convert the C-terminal amino acid residue to a thiohydantoin, i.e., to form a peptidyl thiohydantoin shown in FIG. 5B. Typical reaction conditions are given in Example 2B.

The thiohydantoin is then cleaved off, e.g., by hydrolytic cleavage of the terminal amide bond, under acidic or basic conditions.

Figure 5C:
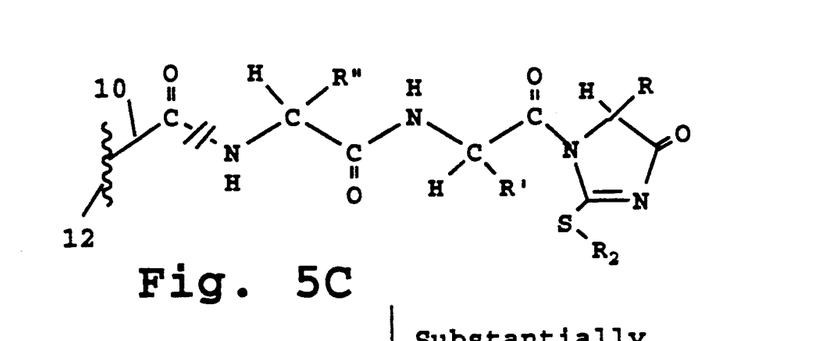

Alternatively, this cleavage can be facilitated by first alkylating the thiohydantoin, under basic conditions, to form an alkylated TH product such as shown in FIG. 5C. Preferred alkylating reagents and conditions are the subject of U.S. Ser. No. 07/775,771, the disclosure of which is incorporated herein by reference. Typical reaction conditions are given Example 3.

Figure 5D:
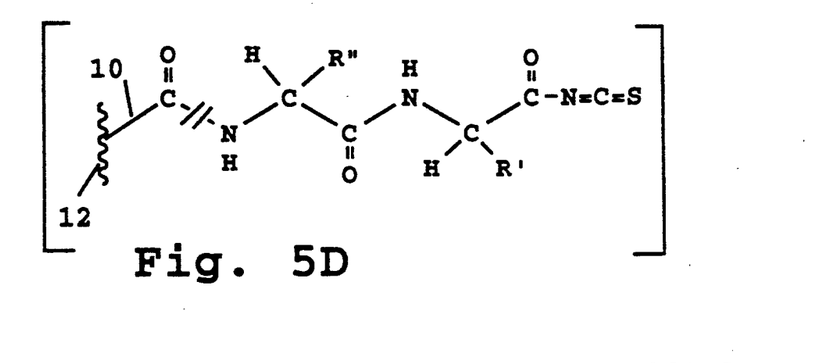
Figure 5E:
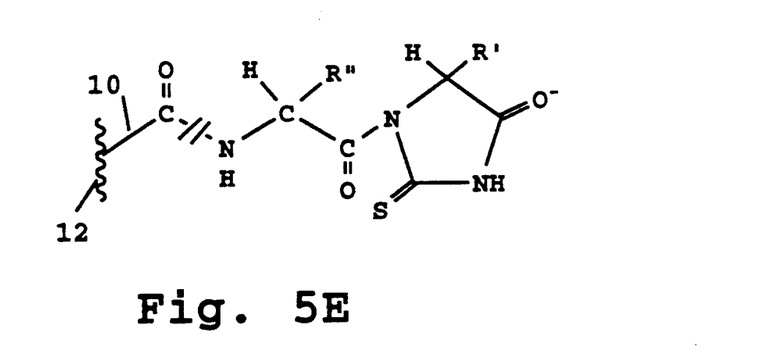

When an alkylating reagent is employed, the cleavage reaction can be performed directly under acidic anhydrous conditions with a thiocyanate anion, as depicted in FIG. 5D. Cleavage in the presence of a thiocyanate reagent, such as TMS-ITC, is preferred since reaction with the thiocyanate reagent under anhydrous acidic conditions is effective to form a new TH at the next-in C-terminal amino acid residue, as illustrated in FIG. 5E. This reaction may proceed through the activated peptidyl NCS intermediate shown in FIG. 5D. Alternatively, the complex of metallothiocyanate and a crown ether under acidic conditions can be used to cleave the alkylated thiohydantoin, with simultaneous formation of the next-in peptidyl thiohydantoin.

In some cases, it may be preferable to cleave the TH from the C-terminal end of the peptide by direct hydrolysis under acidic or basic conditions, to form a C-terminal residue with a free carboxyl group. This residue can then be converted efficiently to the corresponding TH by reaction with a uronium or phosphonium compound, and a thiocyanate reagent, as above.

This latter approach may be preferred, for example, when there is encountered a tertiary amide, such as when proline, which cannot a TH unless the amide bond is first cleaved from the rest of the peptide. Other residues, such as serine, threonine, aspartic acid and glutamic acid, can also be problematic due to the functional groups on the side chains of these residues. However, the use of an uronium compound to rapidly activate synthetic peptides has frequently afforded an improved route to determining a C-terminal amino acid sequence when these residues are present in a peptide.

Studies conducted in support of the present invention indicate that activation with a uronium compound can lead to dehydration of the serine residues. Serine and threonine pose a problem such that sequencing stops at the amino acid immediately prior to these residues in an automated sequencing method. The synthetic peptide "K11(S)V", for example, has a serine at the third residue from the C-terminus. When initial activation of this peptide is performed with Woodward's Reagent K, an HPLC peak for the cleaved valine derivative is observed for the first cycle of chemistry; however, alanine (next-in amino acid after valine, and preceded by serine) and all subsequent amino acids are not observed. The peak size of valine is consistent with the expected yield.

The use of a chlorourinium compound as an activating reagent seems to not only modify the carboxy terminus of the protein or peptide, but also modifies the hydroxyl group of serine (and probably threonine, aspartic acid and glutamic acid). For example, when sequencing K11(S)V using chlorouronium chloride as an activating reagent, a small, but significant peak for alanine is observed as expected in the second cycle. Although preview and lag prevent unambiguous sequence calling, signal for the appropriate residues is occasionally detected up to the fourth residue (cycle), indicating that chlorouronium is in some way modifying the serine residue (mechanism still not understood).

Asp and Glu (carboxylic acid side-chains) are also derivatized by the carboxyl activating reagents. Only a small percent is detected as the unaltered carboxylic acid side chain. It is unknown what the derivatized products are.

The chlorouronium compound is advantageous because it reacts rapidly at room temperature or above, for reaction times of 10 minutes or less, to form an activated ester useful for making a peptidyl-thiohydantoin. As a result, chlorouronium chemistry results in fewer artifact peaks and cleaner chromatography. It is possible using this method to routinely activate protein and peptide in situ on, for example, an Applied Biosystems Sequencer Model 477A in five to ten minutes at room temperature, although the reaction can also be carried out efficiently at, for example, 55° C., consistent with the reaction temperature of subsequent steps. Only one additional bottle position is required for this application. On-line activation with a chlorouronium compound minimizes time consuming sample preparation steps prior to sequencing and is an important enhancement to the C-terminal sequencing chemistry currently under development by ABI.

The above-detailed sequencing technique is readily automated using equipment employed for the automated sequencing of the N-terminal residues of peptides. One embodiment of a device for automatically sequencing a peptide from the C-terminal end employs a surface-immobilized peptide contained in a reaction vessel to which fresh solvent and reagents are added, and from which reaction mixtures and solvent washes are removed. The released amino acid thiohydantoin is extracted from the support and transferred to an on-line HPLC for analysis.

D. Thiocyanate Method

The invention also includes, in a method of forming a thiohydantoin from an N-protected amino acid residue, by activating the carboxyl group of the amino acid, an improvement in which the activated, N-protected amino acid is reacted with a crown ether adduct of a metallothiocyanate.

In one preferred embodiment, the crown ether is an 18-crown-6 ether and the metallothiocynate is a thiocyanate salt of a monovalent cation, such as KSCN, NaSCN, or CsSCN.

Also in a preferred reaction method, the carboxyl group of the N-protected amino acid is activated by reaction with a uronium or phosphonium compound, as described above, and in particular, a halouronium, triflate uronium, or sulfonate uronium compound, or a halophosphonium, triflate phosphonium, or sulfonyl phosphonium compound.

The following examples are presented to illustrate the present invention in more detail and are not to be construed in any way as limiting the scope of the invention.

EXAMPLES

In these examples, the following abbreviations are defined as follows (if not defined, the abbreviations have their generally accepted meanings):

| | |
|---|---|
| Ac | acyl or acetyl |
| DIEA | diisopropylethylamine |
| DITC | 1,4-phenylene diisothiocyanate |
| DSS | disuccinimidyl suberate |
| Fmoc | fluorenylmethoxycarbonyl |
| HBTU | 2-(1H-benzotriazol-1-yl)-1,1,3,3-tetramethyluronium hexafluorophosphate |
| HPLC | high pressure liquid chromatography |
| ITC | isothiocyanate |
| NMP | N-methylpyrrolidone |
| PVDF | polyvinyldifluoride |
| PyBroP | Bromo-tris-pyrrolidino-phosphonium hexafluoro phosphate |
| TFA | trifluoroacetic acid |
| TH | thiohydantoin |
| TLC | thin layer chromatography |
| TMUCl | tetramethylchlorouronium chloride |
| TMS-ITC | trimethylsilyl-isothiocyanate - $(CH_3)_3SiNCS$ |
| TPyClU | tetrahydropyrrolo-2-chlorouronium tetrafluro borate |
| WRK | Woodward's Reagent K (2-Ethyl-5-phenylisoxazolium-3'-sulfonate) 18-crown-6 1,4,7,10,13,16-hexaoxa-cyclooctadecane |

In these examples, TMS-ITC, 18-crown-6, pyridine, and KSCN were purchased from Aldrich Chemical Co. (Milwaukee, Wis.). DSS was purchased from Pierce Chemical (Rockford, Ill.). N-acylated peptides were purchased from Bachem Biosciences, Inc. (Philadelphia, Pa.). PVDF-COOH membrane was obtained from Pall Corporation (Long Island, N.Y.). Unless otherwise indicated, other reagents and peptides were prepared at Applied Biosystems, Inc. (Foster City, Calif.) using standard procedures. $^1H$ NMR spectra were obtained on a 300 MHz Varian spectrometer.

EXAMPLE 1

TH Formation with Free Amino Acids in Solution

A. Chlorouronium Reaction

The chloride salt of TMUCl was prepared following the procedure described by Knorr, et al. [*Tetrahedron Letters*, 30 (25):1927 (1989)]. After synthesis, the chlorouronium chloride crystals were stored in a vacuum desiccator over $P_2O_5$.

The prepared TMUCl chloride readily activated Fmocalanine in solution. In this experiment, 1 mmol of Fmoc-alanine-OH was dissolved in 5 mL of methylene chloride. DIEA (2 equivalents), TMUCl chloride (1 equivalent), and TMS-ITC (1 equivalent) were added to the protected amino acid. The reaction mixture was stirred at room temperature for about 30 minutes, after which the reaction mixture was examined by $^1H$ NMR to determine the presence of thiohydantoin. This study illustrates the rapid synthesis of an amino acid TH in solution using the chlorouronium chloride reagent.

B. Using HBTU Uronium Compound

Approximately 50 mg (0.38 mmol) of Ac-alanine-OH was dissolved in 1 ml of anhydrous acetonitrile. One equivalent of HBTU was added. The reagents did not completely dissolve until 2 equivalents of DIEA were added. After approximately 2 minutes, one equivalent of TMS-ITC was added to the reaction mixture. The reaction was monitored by thin layer chromatography (solvent system was methylene chloride-methanol, 9.5:0.5, v/v). The reaction mixture was allowed to incubate for 20 minutes in a 55° C. heat block. After 20 minutes, another aliquot of the reaction mixture was taken for TLC. Acalanine-TH was independently synthesized, as described in U.S. Ser. No. 07/775,771, and was used as a reference standard for the TLC. After development of the TLC plates, both aliquots of sample indicated product at the same $R_f$ as the standard (presence of product visible under UV lamp).

The reaction mixture was concentrated in a Savant Speed Vac overnight. The sample was then reconstituted in a minimal amount of methylene chloride:methanol (9.5:0.5, v/v) and purified using a TLC prep plate (silica gel). After development, the appropriate band was scraped from the TLC plate, and extracted with methanol/methylene chloride 1:1. The product was analyzed with a $^1$H NMR spectrometer and confirmed to be acetyl-alanine-TH.

C. HBTU Reaction with Peptides

Similar tests for reactivity using HBTU were performed on the following synthetic polypeptides:
Ac-SEQ ID NO:1-OH; Ac-SEQ ID NO:2-OH; A14G, Fmoc-SEQ ID NO:3; and G12Y, Fmoc-SEQ ID NO:4-OH.

A14G and G12Y were first covalently attached to a polystyrene support, as described in Example 2 below.

The results of the above experiments established that HBTU can generate some thiohydantoin product for the one amino acid examined (Ac-Ala-OH). However, HBTU was only poorly effective or was ineffective in forming thiohydantoin from polypeptides. This may attributed to poor reactivity of the activated (HOBt) ester and/or competition between the HOBt and thiocyanate anions for reaction with the uronium activated ester.

EXAMPLE 2

Formation of Immobilized Peptidyl Thiohydantoins with TMUCl Chloride

A. Synthesis and Immobilization of Peptide A14G

The polypeptide A14G (defined in Example 1) was synthesized on an Applied Biosystems, Inc. Model 431A Peptide Synthesizer using the standard Fastmoc TM cycles. Deprotection and cleavage were performed by standard methods, and the peptide was characterized by HPLC and amino acid analysis.

Peptide A14G was attached to polystyrene beads as follows: 100 mg of aminomethyl polystyrene beads (26 μmol NH$_2$/g) (Applied Biosystems, Inc.) were activated in 720 μL NMP with 15 mg DSS linker, 40 μL DIEA and 40 μL pyridine. The beads and activation solution were shaken for 1 hour at room temperature, after which the beads were washed three times with NMP. The synthetic peptide, A14G (15 mg) was dissolved in 360 μL of NMP, 40 μL pyridine and 40 μL DIEA, and was then added to the activated beads. The beads and peptide solution were shaken for at least 12 hours at room temperature. The beads were then washed three times each with NMP and acetonitrile, and dried in a Speed Vac concentrator.

Other examples of immobilization of peptides on resin and glass beads are presented in U.S. Ser. No. 07/775,771, which disclosure is incorporated herein by reference, and are suitable for practice of the present invention.

B. Reaction of TMUCl Chloride with Immobilized Peptide

TMUCl chloride (0.5–1 mmol) was dissolved in 2 mL of acetonitrile with 1–2 molar equivalents of DIEA. Approximately 750 μL of this solution was combined in an Eppendorf tube with about 20 mg of the A14G-polystyrene beads prepared above. Approximately 1–2 molar equivalents of TMS-ITC were added immediately following the addition of the chlorouronium solution. The tube was closed, vortexed for several seconds, and placed in a 60° C. heat block for 30 minutes. The polystyrene beads were washed consecutively, twice with acetonitrile, twice with acetonitrile:water (1:1, v/v), and again twice with acetonitrile. The beads were dried in a Speed Vac (15–30 minutes).

Approximately 1 mg of polystyrene resin with bound-A14G-TH was sequenced from the C-terminus for 6 cycles using an Applied Biosystems, Inc. Model 477A Protein/Peptide Sequencer. Conditions for the C-terminal sequencing procedure are described in U.S. Ser. No. 07/775,771. The yield of the initial TH formation in the peptides was between 50–100%.

EXAMPLE 3

Automated Formation and Sequencing of C-terminal Thiohydantoin on Proteins and Peptides with Single Use of a Chlorouronium Chloride Proteins and peptides attached to a solid support (as described above) were derivatized to C-terminal thiohydantoins and then sequenced from the C-terminus on an Applied Biosystems Model 477A Protein Sequencer. In these experiments, a 10% solution of the TMUCl chloride in acetonitrile was loaded in the X1 position of the Model 477A. A modified "Begin" cycle was implemented to deliver an aliquot of 10% DIEA in acetonitrile, an aliquot of 10% TMUCl chloride solution, and an aliquot of 10% TMS-ITC in acetonitrile. This was followed by a 5–10 minute pause, after which an additional aliquot of TMS-ITC was delivered. The reaction temperature was 55° C. Using this protocol, C-terminal thiohydantoin formation was achieved in less than 20 minutes for each peptide and protein studied.

The activation reagents were rinsed from the reaction, cartridge with acetonitrile following the reaction and sequencing was performed (as described in U.S. Ser. No. 07/775,771). In this procedure, the C-terminal thiohydantoin is reacted with an alkylating reagent to make the thiohydantoin a better leaving group. TMS-ITC (or a metallothiocyanate crown ether complex) and TFA vapor are then used to cleave the thiohydantoin adduct from the remaining peptide and form a thiohydantoin of the next-in amino acid residue.

In one typical procedure, the immobilized peptidyl TH is treated with base, e.g., DIEA, and an alkylating reagent, such as bromomethylnaphthalene, and the reaction is allowed to proceed for 20 minutes at 55° C. TMS-ITC and TFA vapor are then used to cleave the alkylated thiohydantoin adduct from the remaining (residual) immobilized peptide, forming at the same time, a TH of the next-in C-terminal amino acid residue.

Figure 6:
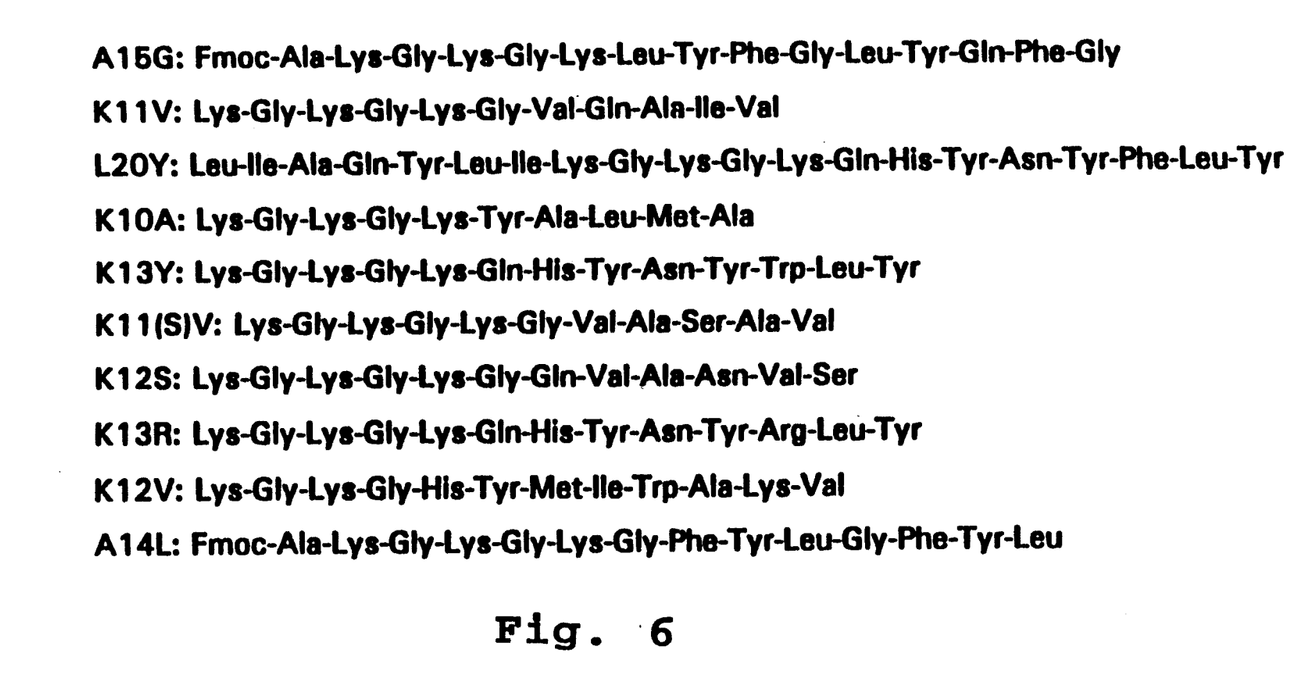
FIG. 6 shows the sequences of a number of synthetic peptides discussed in the specification.

This method for C-terminal sequencing (on-line thiohydantoin derivatization for the "Begin" cycle only, followed by repeated cycles of alkylation and cleavage/re-formation of the next-in thiohydantoin) has been used to successfully determine 5 residues of the C-terminal sequence of horse apomyoglobin (Sigma Chemical; St. Louis, Mo.) and up to 3 residues of cytochrome-c (Sigma) covalently attached to DITC glass beads. Also, the C-terminal residue of β-lactoglobulin (Sigma) and 4 residues of lysozyme (Sigma) immobilized on functionalized PVDF (PVDF-COOH) have been identified using this method The C-terminal sequence of each of the following synthetic peptides (FIG. 6) has been successfully sequenced with this method: A15G, Fmoc-SEQ ID NO:5; K11V, SEQ ID NO:6; L20Y, SEQ ID NO:7; K10A, SEQ ID NO:8; K13Y, SEQ ID NO:9; K11(S)V, SEQ ID NO:10; K12S, SEQ ID NO:11; K13R, SEQ ID NO:12; K12V, SEQ ID NO:13; and A14L, Fmoc-SEQ ID NO:14.

The number of cycles successfully performed using TMUCl chloride in a single activation step are indicated (in parentheses) for the respective peptides:
A15G (9), K11V (6), L20Y (8), K10A (4), K13Y (4), K11(S)V (2+), K12S (6), K13R (3+), K12V (4), A14L (7).

A second uronium salt was also employed to activate several synthetic peptides. The salt, tetrahydropyrrolochlorouronium tetrafluoroborate (TPyClU), commercially available from SNPE, Inc. (Princeton, N.J.), gave similar results to those obtained for TMUCl chloride, i.e., yields of the C-terminal amino acid TH between 50–100%. However, the TPyClU tetrafluoroborate has generally better handling properties due to it being less hygroscopic than the chloride salt. Synthetic peptides successfully sequenced using TPyClU to activate only the first C-terminal residue were: K11V (5), K11(S)V (2), and A15G (6), with the number of cycles indicated in parentheses.

Cleaved thiohydantoin adducts were isolated and identified by the methods presented in U.S. Ser. No. 07/775,771, which are suitable for practice of the present invention.

EXAMPLE 4

Automated Formation and Sequencing of C-Terminal Thiohydantoin on Peptides with Repeated Activation with a Chlorouronium Chloride An alternative to the method described above in Example 3 can be employed in which a terminal carboxyl group is generated upon cleavage of each thiohydantoin from the peptide and the C-terminus is reactivated each time using a uronium compound. In this method, the alkylated-thiohydantoin can be cleaved from the protein or peptide using an acid, e.g., TFA, absent an isothiocyanate source. When TMS-ITC is omitted from the cleavage reaction, the alkylated-thiohydantoin is released for detection; however, the truncated protein or peptide is returned to a moiety that can be activated with chlorouronium chloride.

A sequencing cycle using this protocol preferably involves the following steps: a) activation of the carboxyl group with a chlorouronium chloride, DIEA, and TMS-ITC to form a thiohydantoin; b) alkylation of the thiohydantoin using a bromomethylnaphthalene reagent in the presence of DIEA; and c) cleavage of the alkylated thiohydantoin using TFA vapor which leads to a moiety that converts to a free carboxyl group on the truncated polypeptide during washes.

This sequencing method has been used to sequence 4 cycles of a synthetic peptide (K11V) covalently attached to polystyrene beads using TMUCl chloride in repetitive reactivations. Generally, however, this method of TFA cleavage followed by chlorouronium re-activation at the beginning of each degradation cycle is found to be less efficient than simultaneous cleavage and thiohydantoin regeneration as described above and in U.S. Ser. No. 07/775,771.

EXAMPLE 5

Automated Formation of C-terminal Thiohydantoins Using Phosphonium Compound.

The hexafluorophosphate salt of PyBroP, commercially available from Calbiochem (La Jolla, Calif.), was used to generate C-terminal thiohydantoins from several synthetic peptides during on-instrument activation. In these experiments, the only modification of the methods described above using a chlorouronium chloride entailed replacing the X1 bottle (10% TMUCl chloride in acetonitrile) with 10% PyBroP in acetonitrile. The following peptides were successfully converted to their C-terminal thiohydantoins and subsequently sequenced for the number of cycles in parentheses: K11V (5), L20Y (8), and A15G (5). The numbers in parentheses indicate the number of cycles successfully performed.

EXAMPLE 6

Preparation of 18-Crown-6 Adduct of Potassium Thiocyanate

Potassium thiocyanate (0.325 g, 0.003 mol) and 18-crown-6 (0.794 g, 0.003 mol) were dried over phosphorus pentoxide in a vacuum desiccator for more than 12 hours. The mixture was then dissolved in 10 mL of dry acetonitrile (HPLC grade, Applied Biosystems, Inc.). This solution was installed on an Applied Biosystems Model 477A Protein Sequencer.

It was observed that potassium thiocyanate is rendered soluble in acetonitrile and the "naked" isothiocyanate anion has a significantly increased nucleophilicity upon complexation of the potassium ion with 18-crown-6. Also, the reagent is found to be much less moisture sensitive than TMS-ITC, it is noncorrosive, the preparation and handling of this reagent are convenient and safe, and the 18-crown-6 adduct is stable for at least 10 days when installed on an automated sequencer (in an amber bottle and under argon).

EXAMPLE 7

C-Terminal Sequencing of Peptides Using KSCN/18-crown-6 as Cleaving Reagent

The peptide G12Y was synthesized on an Applied Biosystems Model 431A Peptide Synthesizer and was attached to polystyrene resin beads using the procedure described above in Example 2. The immobilized peptide was transformed into the thiohydantoin derivative using Woodward's Reagent K and TMS-ITC, as described in U.S. 5,051,368 and U.S. Ser. No. 07/775,771, and was sequenced with an Applied Biosystems Model 477A Protein Sequencer. Alkylation of the peptidyl thiohydantoin with 2-bromomethyl-naphthalene in the presence of DIEA was followed by washing the sample with acetonitrile.

The cleaving reagent (0.3 M KSCN/18-crown-6 solution in acetonitrile) was then delivered until the resin became well saturated (approximately 3 seconds) After a ten second pause, the excess solution was removed with argon (5 seconds) followed by TFA vapor, according to procedures described in U.S. Ser. No. 07/775,771. Four consecutive sequencing cycles were performed and the expected peaks of the cleaved amino acid S-alkylated thiohydantoins were observed on HPLC chromatograms.

A second peptide, K10A, was covalently attached to a PVDF-COOH membrane. A 0.5 mg portion of the membrane containing the immobilized peptide (3 nmol) was placed in the reaction chamber of an Applied Biosystems 477A Protein Sequencer and activated with TMUCl chloride, as described above in Example 3. The activated peptide was then treated with 0.3 M KSCN/18-crown-6 solution in acetonitrile in the presence of DIEA. The KSCN/18-crown-6 solution was delivered twice for 1 second with each delivery followed by a 300 second and a 100 second pause, respectively, to permit the thiohydantoin formation reaction to proceed. The sample was washed with acetonitrile and the TH derivative was subjected to C-terminal sequencing as described in Example 3. Four successful cycles were performed giving interpretable peaks on HPLC chromatograms.

Although the present invention has been described in some detail by way of illustration and example for purposes of clarity and understanding, it should be apparent that a number of variations and modifications can be practiced without departing from the scope of the invention.

---

It is claimed:

1. A method of converting an N-protected amino acid to the corresponding amino acid thiohydantoin, comprising
reacting the N-protected amino acid, in the presence of a base, with (a) a uronium compound selected from the group consisting of a halouronium, pseudohaluronium, tosyl uronium, triflate uronium, and sulfonyl uronium, or (b) a phosphonium compound selected from the group consisting of a halophosphonium, tosyl phosphonium, triflate phosphonium, and sulfonyl phosphonium, to form an activated carboxylate ester, and reacting said activated ester with a thiocyanate reagent under conditions effective to form an amino acid thiohydantoin.

2. The method of claim 1, wherein said reacting of the N-protected amino acid with a uronium or phosphonium compound is carried out in the presence of said thiocyante reagent.

3. The method of claim 1, wherein the uronium compound is a 2-halouronium salt.

4. The method of claim 3, wherein the uronium compound is a 1,1,3,3-tetrasubstituted uronium salt.

5. The method of claim 1, wherein the phosphonium compound is a P-halophosphonium salt.

6. The method of claim 5, wherein the phosphonium compound is a tris(dialkylamino) phosphonium salt.

7. The method of claim 1, wherein the thiocyanate reagent is selected from the group comprising a silylisothiocyanate, a pyridinium thiocyanate, and a complex of a metallothiocyanate and a crown ether.

8. The method of claim 7, wherein the silylisothiocyanate is trimethylsilylisothiocyanate and the complex is composed of an 18-crown-6 ether and potassium thiocyanate.

9. The method of claim 1, wherein the N-protected amino acid is the C-terminal amino acid of a polypeptide immobilized on a solid support.

10. The method of claim 9, for use in identifying the C-terminal amino acid residue of a polypeptide, further comprising:
  (a) contacting the formed amino acid thiohydantoin with a cleaving agent under conditions effective to release a deprotected amino acid thiohydantoin from residual peptide; and
  (b) isolating and identifying the deprotected amino acid thiohydantoin, thereby identifying the C-terminal residue of the polypeptide.

11. The method of claim 10, wherein said contacting includes alkylating the thiohydantoin, and contacting the alkylated thiohydantoin, under anhydrous acidic conditions, with a thiocyanate reagent, under conditions effective to form a thiohydantoin at the C-terminus of the residual peptide.

12. In a method of forming a thiohydantoin from an N-protected amino acid residue, which includes the step of reacting the residue with a carboxyl activating agent, and with a thiocyanate, the improvement comprising employing as the isothiocyante, a complex of a metallothiocyanate and a crown ether.

13. The method of claim 12, wherein the complex is composed of an 18-crown-6 ether and potassium isothiocyanate.

14. The method of claim 12, wherein the carboxyl activating agent is (a) a uronium compound selected from the group consisting of a halouronium, pseudohalouronium, triflate uronium, and sulfonate uronium, or (b) a phosphonium compound selected from the group consisting of a halophosphonium, pseudohalouronium, triflate phosphonium, and sulfonate phosphonium.

* * * * *